United States Patent [19]

Winter et al.

[11] Patent Number: 5,350,817

[45] Date of Patent: Sep. 27, 1994

[54] PROCESS FOR THE PREPARATION OF POLYOLEFINS HAVING A BROAD MOLECULAR WEIGHT DISTRIBUTION

[75] Inventors: Andreas Winter, Glashütten; Volker Dolle, Kelkheim am Taunus; Walter Spaleck, Liederbach, all of Fed. Rep. of Germany

[73] Assignee: Hoechst AG, Frankfurt, Fed. Rep. of Germany

[21] Appl. No.: 119,893

[22] Filed: Sep. 10, 1993

Related U.S. Application Data

[63] Continuation of Ser. No. 888,047, May 22, 1992, abandoned.

[30] Foreign Application Priority Data

May 27, 1991 [DE] Fed. Rep. of Germany ....... 4117259

[51] Int. Cl.$^5$ ................................ C08F 4/64
[52] U.S. Cl. .................. 526/119; 526/118; 526/127; 526/153; 526/160; 526/352; 502/117; 502/155
[58] Field of Search ............... 526/118, 119, 107, 160, 526/153

[56] References Cited

U.S. PATENT DOCUMENTS

| | | | |
|---|---|---|---|
| 4,849,487 | 7/1989 | Kaminsky et al. | 526/160 |
| 4,975,403 | 12/1990 | Ewen | 526/160 |
| 5,001,205 | 3/1991 | Hoel | 526/160 |

FOREIGN PATENT DOCUMENTS

| | | |
|---|---|---|
| 2017190 | 11/1990 | Canada . |
| 0387691 | 9/1909 | European Pat. Off. . |
| 0128045 | 12/1984 | European Pat. Off. . |
| 0128046 | 12/1984 | European Pat. Off. . |
| 0226463 | 6/1987 | European Pat. Off. . |
| 0302424 | 2/1989 | European Pat. Off. . |
| 0310734 | 4/1989 | European Pat. Off. . |
| 0355439 | 2/1990 | European Pat. Off. . |
| 0399348 | 11/1990 | European Pat. Off. . |
| 3640924 | 6/1988 | Fed. Rep. of Germany . |
| 88/5769 | 8/1988 | South Africa . |
| 89/5770 | 4/1990 | South Africa . |
| 90/1845 | 11/1990 | South Africa . |

OTHER PUBLICATIONS

Giannetti, E., et al., *J. of Polymer Science: Polymer Chem. Ed.* 23:2117-2134 (1985).

Primary Examiner—Joseph L. Schofer
Assistant Examiner—David Wu
Attorney, Agent, or Firm—Connolly & Hutz

[57] ABSTRACT

Polyolefins having a molecular weight distribution $M_w/M_n$ of $\geq 3$ and which may be monomodal, bimodal or multimodal are obtained by polymerization or copolymerization of olefins of the formula RCH=CHR, in which a catalyst system comprising an aluminoxane and a transition-metal component (metallocene) is used, the transition-metal component comprising at least one zirconocene of the formula I

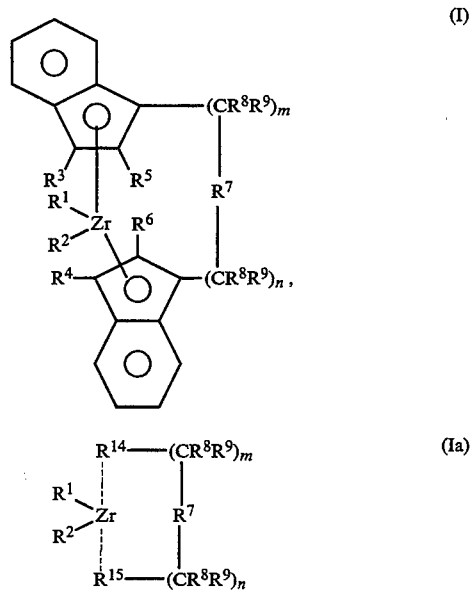

and at least one zirconocene of the formula Ia or alternatively at least 2 zirconocenes of the formula I.

17 Claims, No Drawings

PROCESS FOR THE PREPARATION OF POLYOLEFINS HAVING A BROAD MOLECULAR WEIGHT DISTRIBUTION

This is a continuation of our copending application, U.S. Ser. No. 07/888,047, filed May 22, 1992, now abandoned.

It is known that metallocene catalysts in combination with aluminoxanes are capable of polymerizing olefins to give polyolefins having a narrow molecular weight distribution ($M_w/M_n$ of 2-3) (J. Polym. Sci., Pol. Chem. Ed. 23 (1985) 2117; EP-A 302 424). Polyolefins of this type with a narrow distribution are suitable, for example, for applications in precision injection molding, injection molding in general and for the production of fibers. For numerous applications, such as, for example, thermoforming, extrusion, blow molding and for the production of polyolefin foams and films, broader or bimodal molecular weight distributions are required.

For polyethylene, it has been proposed to achieve such products by using two or more metallocene catalysts in the polymerization (EP-A 128 045); however, the systems described are achiral catalysts and would give atactic polypropylene on polymermization of propene. However, atactic polypropylene is unsuitable as a structural material.

The preparation of stereoblock polypropylene where $M_w/M_n$ is 13-15 is disclosed in DE-A 3 640 924. These catalyst systems are likewise unsuitable for the formation of polyolefins of high tacticity. Furthermore, the metallocene activities which can be achieved at industrially relevant polymerization temperatures and the molecular weights of polymer products are too low. In addition, the proposed catalysts give only an atactic polymer at such polymerization temperatures.

EP-A 310 734 proposes catalyst systems comprising a mixture of a hafnocene and a zirconocene for the preparation of polypropylene. Products have broad to bimodal distributions where $M_w/M_n$ is from 3.7 to 10.3

If only the hafnocene catalyst is used, polypropylene with a broad distribution is obtained at a certain polymerization temperature, according to EP-A 355 439.

Syndiotactic polypropylene having a broad distribution is described in EP-A 387 691 ($M_w/M_n$ up to 6.4) if a hafnocene is used.

These processes have the common disadvantages of hafnium catalyst costs which are too high for industrial applications, together with a low polymerization activity, which additionally makes it necessary to carry out thorough, high-cost purification of the prepared polymer to remove catalyst residues.

The object was thus to find a catalyst system and a process by means of which polyolefins having a broad, bimodal or multimodal distribution can be prepared and which avoid the disadvantages known from the prior art.

The object is achieved by using a catalyst system comprising at least two stereorigid zirconocenes and an aluminum compound as cocatalyst.

The invention thus relates to a process for the preparation of a polyolefin which has a molecular weight distribution $M_w/M_n$ of $\geq 3.0$ and which may be monomodal, bimodal or multimodal, by polymerization or copolymerization of an olefin of the formula $R^aCH\!=\!CHR^b$ in which $R^a$ and $R^b$ are identical or different and a hydrogen atom or a alkyl radical having 1 to 14 carbon atoms, or $R^a$ and $R^b$, together with the atoms connecting them, can form a ring, at a temperature of from $-60°$ to $200°$ C., at a pressure of from 0.5 to 100 bar, in solution, in suspension or in the gas phase, in the presence of a catalyst comprising a transition-metal component (metallocene) and an aluminoxane of the formula II

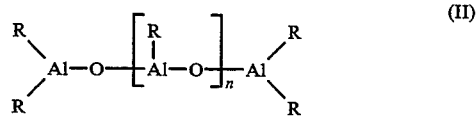

for the linear type and/or of the formula III

for the cyclic type, where, in the formulae II and III, the radicals R may be identical or different and are a $C_1$-$C_6$-alkyl group, a $C_1$-$C_6$-fluoroalkyl group, a $C_6$-$C_{18}$-aryl group, a $C_1$-$C_6$-fluoroaryl group or a hydrogen, and n is an integer from 0 to 50, or, instead of the aluminoxane, comprises a mixture of an aluminoxane of the formula II and/or of the formula III with a compound $AlR_3$, which comprises using, as the transition-metal component, at least one zirconocene of the formula I and at least one zirconocene of the formula Ia or alternatively at least 2 zirconocenes of the formula I

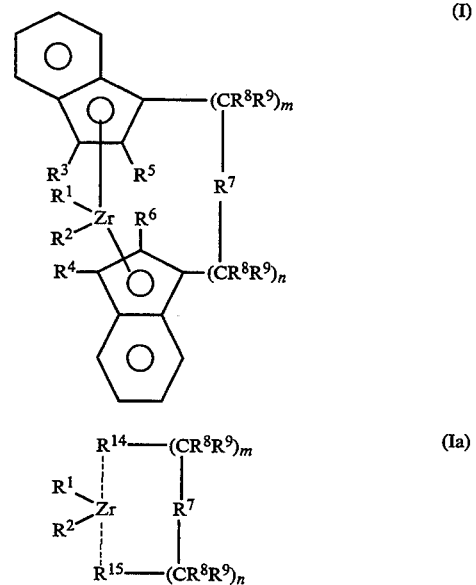

in which $R^1$ and $R^2$ are identical or different and are a hydrogen atom, a $C_1$-$C_{10}$-alkyl group, a $C_1$-$C_{10}$-alkoxy group, a $C_6$-$C_{10}$-aryl group, a $C_6$-$C_{10}$-aryloxy group, a $C_2$-$C_{10}$alkenyl group, a $C_7$-$C_{40}$-arylalkyl group, a $C_7$-$C_{40}$-alkylaryl group, a $C_8$-$C_{40}$-arylalkenyl group or a halogen atom, $R^3$ and $R^4$ are identical or different and are a hydrogen atom, a halogen atom, a $C_1$-$C_{10}$-alkyl group, which may be halogenated, a $C_6$-$C_{10}$-aryl group, or a $-NR_2^{10}$, $-SR^{10}$, $-OSiR_3^{10}$, $-SiR_3^{10}$ or —PR$_2^{10}$ radical in which R$^{10}$ is a halogen atom, a C$_1$–C$_{10}$-alkyl group or a C$_6$–C$_{10}$-aryl group, R$^5$ and R$^6$ are identical or different and are as defined for R$^3$ and R$^4$, with the proviso that R$^5$ and R$^6$ are not hydrogen, R$^7$ is

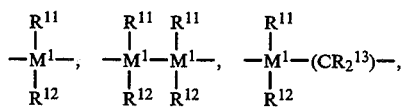

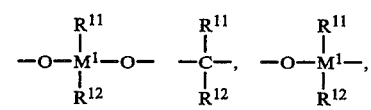

=BR$^{11}$, =AlR$^{11}$, —Ge—, —Sn, —O—, —S—, =SO, =SO$_2$, =NR$^{11}$, =CO, =PR$^{11}$ or =P(O)R$^{11}$, where R$^{11}$, R$^{12}$ and R$^{13}$ are identical or different and are a hydrogen atom, a halogen atom, a C$_1$–C$_{10}$-alkyl group, a C$_1$–C$_{10}$-fluoroalkyl group, a C$_6$–C$_{10}$-aryl group, a C$_6$–C$_{10}$-fluoroaryl group, a C$_1$–C$_{10}$-alkoxy group, a C$_2$–C$_{10}$-alkenyl group, a C$_7$–C$_{40}$-arylalkyl group, a C$_8$–C$_{40}$-arylalkenyl group or a C$_7$–C$_{40}$-alkylaryl group, or R$^{11}$ and R$^{12}$ or R$^{11}$ and R$^{13}$, together with the atoms connecting them, in each case form a ring, and M$^1$ is silicon, germanium or tin, R$^8$ and R$^9$ are identical or different and are as defined for R$^{11}$, R$^{14}$ and R$^{15}$ are identical or different and are a monocyclic or polycyclic hydrocarbon radical which can form a sandwich structure together with the zirconium atom, and m and n are identical or different and are zero, 1 or 2, where m plus n is zero, 1 or 2.

Alkyl is straight-chain or branched alkyl. Halogen (halogenated) refers to fluorine, chlorine, bromine or iodine, preferably fluorine or chlorine.

R$^1$ and R$^2$ are identical or different and are a hydrogen atom, a C$_1$–C$_{10}$-, preferably C$_1$–C$_3$-alkyl group, a C$_1$–C$_{10}$-, preferably C$_1$–C$_3$-alkoxy group, a C$_6$–C$_{10}$-, preferably C$_6$–C$_8$-aryl group, a C$_6$–C$_{10}$-, preferably C$_6$–C$_8$-aryloxy group, a C$_2$–C$_{10}$-, preferably C$_2$–C$_4$-alkenyl group, a C$_7$–C$_{40}$-, preferably C$_7$–C$_{10}$-arylalkyl group, a C$_8$–C$_{40}$-, preferably C$_7$–C$_{12}$-alkylaryl group, a C$_8$–C$_{40}$-, preferably C$_8$–C$_{12}$-arylalkenyl group, or a halogen atom, preferably chlorine.

R$^3$ and R$^4$ are identical or different and are a hydrogen atom, a halogen atom, preferably fluorine, chlorine or bromine atom, a C$_1$–C$_{10}$-, preferably C$_1$–C$_4$-alkyl group, which may be halogenated, a C$_6$–C$_{10}$-, preferably C$_6$–C$_8$-aryl group, a —NR$_2^{10}$, —SR$^{10}$, —OSiR$_3^{10}$, SiR$_3^{10}$ or —PR$_2^{10}$ radical in which R$^{10}$ is a halogen atom preferably a chlorine atom, or a C$_1$–C$_{10}$-, preferably C$_1$–C$_3$-alkyl group or a C$_6$–C$_{10}$-, preferably C$_6$–C$_8$-aryl group. R$^3$ and R$^4$ are particularly preferably hydrogen.

R$^5$ and R$^6$ are identical or different, preferably identical, and are as defined for R$^3$ and R$^4$, with the proviso that R$^5$ and R$^6$ cannot be hydrogen. R$^5$ and R$^6$ are preferably (C$_1$–C$_4$)-alkyl, which may be halogenated, such as methyl, ethyl, propyl, isopropyl, butyl, isobutyl or trifluoromethyl, in particular methyl.

R$^7$ is

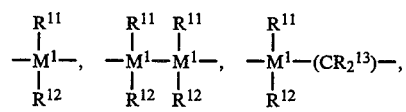

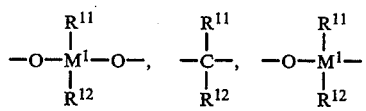

=BR$^{11}$, =AlR$^{11}$, —Ge—, —Sn, —O—, —S—, =SO, =SO$_2$, =NR$^{11}$, =CO, =PR$^{11}$ or =P(O)R$^{11}$, where R$^{11}$, R$^{12}$ and R$^{13}$ are identical or different and are hydrogen atoms, halogen atoms, a C$_1$–C$_{10}$-, preferably C$_1$–C$_4$-alkyl group, in particular methyl group, a C$_1$–C$_{10}$-fluoroalkyl group, preferably CF$_3$ group, a C$_6$–C$_{10}$-, preferably C$_6$–C$_8$-aryl group, a C$_6$–C$_{10}$-fluoroaryl group, preferably pentafluorophenyl group, a C$_1$–C$_{10}$-, preferably C$_1$–C$_4$-alkoxy group, in particular methoxy group, a C$_2$–C$_{10}$-, preferably C$_2$–C$_4$-alkenyl group, C$_7$–C$_{40}$-, preferably C$_7$–C$_{10}$-arylalkyl group, a C$_8$–C$_{40}$-, preferably C$_8$–C$_{12}$-arylalkenyl group, or a C$_7$–C$_{40}$-, preferably C$_7$–C$_{12}$-alkylaryl group, or R$^{11}$ and R$^{12}$ or R$^{11}$ and R$^{13}$, together with the atoms connecting them, in each case form a ring.

M$^1$ is silicon, germanium or tin, preferably silicon or germanium.

R$^7$ is preferably =CR$^{11}$R$^2$, =SiR$^{11}$R$^{12}$, =GeR$^{11}$R$^{12}$, —O—, —S—, =SO, =PR$^{11}$ or =P(O)R$^{11}$.

R$^8$ and R$^9$ are identical or different and are as defined for R$^{11}$.

m and n are identical or different and are zero, 1 or 2, preferably zero or 1, where m plus n is zero, 1 or 2, preferably zero or 1.

R$^{14}$ and R$^{15}$ are preferably fluorenyl, indenyl or cyclopentadienyl, it being possible for these parent structures also to carry additional substituents as defined for R$^{11}$.

Particularly preferred metallocenes are thus those in which, in the formula I, R$^1$ and R$^2$ are identical or different and are methyl or chlorine, R$^3$ and R$^4$ are hydrogen, R$^5$ and R$^6$ are identical or different and are methyl, ethyl or trifluoromethyl, R$^7$ is a

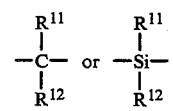

radical, and n plus m is zero or 1, in particular the compounds listed in the working examples.

Of the compounds I mentioned in the working examples, rac-dimethylsilyl(2-methyl-1-indenyl)$_2$zirconium dichloride, rac-ethylene(2-methyl-1-indenyl)$_2$zirconium dichloride, rac-diphenylsilyl(2-methyl-1-indenyl)$_2$ zirconium dichloride, rac-methylethylene(2-methyl-1-indenyl)$_2$zirconium dichloride and racphenyl(methyl)-silyl(2-methyl-1-indenyl)$_2$zirconium dichloride are of particular importance.

The particularly preferred metallocenes of the formula Ia are those in which R$^1$ and R$^2$ are identical or different and are methyl or chlorine, R$^7$ is a

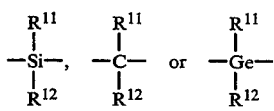

radical n+m is zero or 1 and

R$^{14}$ and R$^{15}$ are identical or different and are fluorenyl, indenyl or substituted cyclopentadienyl, in particular the compounds Ia listed in the working examples.

Of particular importance are thus rac-phenyl(methyl)silyl(indenyl)$_2$zirconium dichloride, diphenylmethylene(9-fluorenyl) (cyclopentadienyl) zirconium dichloride, isopropylidene (9-fluorenyl) (cyclopentadienyl) zirconium dichloride, rac-dimethylsilyl (2,3,5-trimethyl-1-cyclopentadienyl)$_2$zirconium dichloride, rac-dimethylsilyl(indenyl)$_2$zirconium dichloride, rac-dimethylgermyl(indenyl)$_2$zirconium dichloride, rac-dimethylsilyl(indenyl)$_2$dimethylzirconium, rac-phenyl(vinyl)silyl(indenyl)$_2$zirconium dichloride,

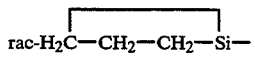

rac-dimethylsilyl (2,4-dimethylcyclopentadienyl)$_2$zirconium dichloride, racisopropylidene(idenyl)$_2$zirconium dichloride, racdimethylsilyl (2-methyl-4,5,6,7-tetrahydro-1-indenyl)$_2$zirconium dichloride, rac-ethylene(indenyl)$_2$zirconium dichloride, rac-methylene(3-t-butyl-1-cyclopentadienyl)$_2$zirconium dichloride and rac-dimethylsilyl(4,7-dimethyl-1-idenyl)-$_2$zirconium dichloride.

The metallocenes having C$_s$ symmetry (subgroup of compounds of the formula Ia; for example R$^{11}$R$^{12}$C(fluorenyl)(cyclopentadienyl)dimethylzirconium) are employed for the preparation of the syndiotactic block in the polyolefin.

For the purposes of the present invention, the term C$_s$ symmetry means that the corresponding metallocenes have a mirror plane perpendicular to the plane passing through Zr, R$^1$ and R$^2$. The bisecting line of the angle ⟨R$^1$-Zr-R$^2$ extends in this mirror plane. This consideration of symmetry is restricted to part of the zirconocene molecule, i.e. the —(CR$^8$R$^9$)$_n$—R$^7$—(CR$^8$R$^9$-)$_m$— bridge is not taken into account. Furthermore, the term C$_s$ symmetry should be understood in formal or idealized terms. Thus, for example, shifts in said moiety which may be caused by the bridge and can only be explained via the structure are not considered for the purposes of the present invention.

The chiral metallocenes are employed as racemates for the preparation of highly isotactic polyolefins. However, it is also possible to use the pure R- or S-form. These pure stereoisomeric forms allow preparation of an optically active polymer. However, the meso-form of the metallocenes should be removed since the polymerization-active center (the metal atom) in these compounds is no longer chiral due to mirror symmetry at the central metal and can therefore not produce any highly isotactic polymer. If the meso-form is not removed, atactic polymer is formed alongside isotactic polymer. For certain applications—soft moldings for example—this may be thoroughly desirable.

The principle of resolution of stereoisomers is known.

The metallocenes I and Ia can be prepared by the principle of the following reaction scheme:

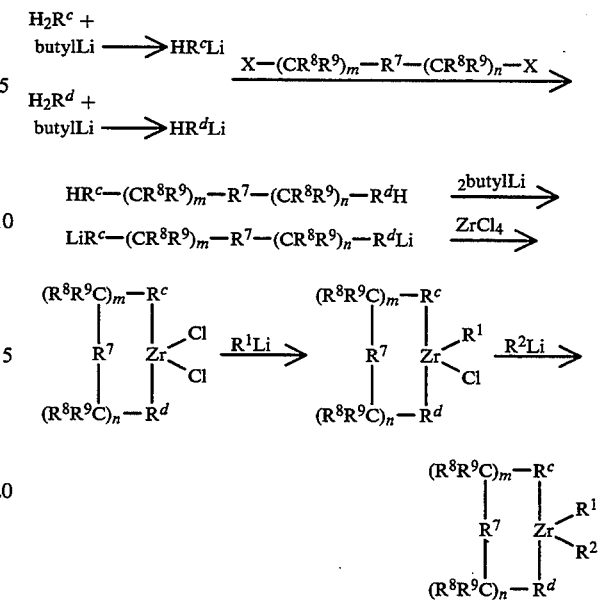

X = Cl, Br, I or O-tosyl;

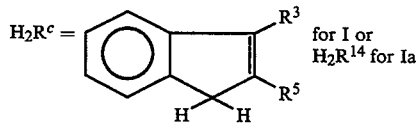
for I or H$_2$R$^{14}$ for Ia

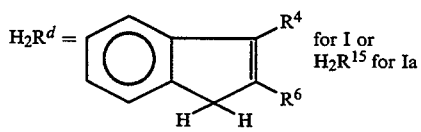
for I or H$_2$R$^{15}$ for Ia or

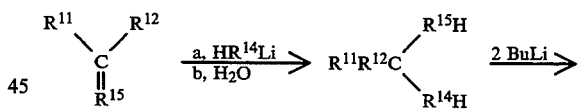

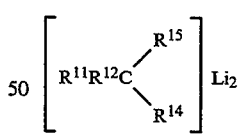

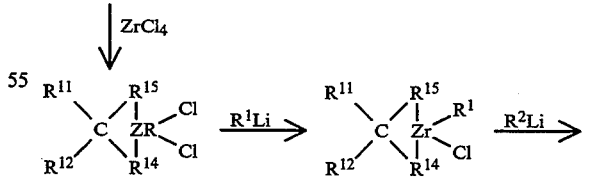

(cf. Journal of Organomet. Chem. (1985) 63–67 and EP-A 320762).

The choice of the metallocenes for the polymerization of olefins to give polyolefins having a broad or multimodal distribution can take place by means of a test polymerization for each metallocene.

In this test, the olefin is polymerized to the polyolefin and the mean molecular weight $M_w$ thereof and the molecular weight distribution $M_w/M_n$ thereof are determined by means of gel permeation chromatography. Depending on the desired molecular weight distribution, the metallocenes are then combined.

Taking into account the polymerization activities, it is then possible, by means of computer simulation of the combined gel permeation curves, to directly produce any desired molecular weight distribution via the type of metallocenes and via the ratio of the amounts of the metallocenes to one another.

The number of zirconocenes to be used according to the invention is preferably 2 or 3, in particular 2. However, it is also possible to use a greater number (such as, for example, 4 or 5) in any desired combination of I and Ia.

By including the polymerization activities and molecular weights at various polymerization temperatures, in the presence of hydrogen as molecular weight regulator or in the presence of comonomers, the computer simulation model can be further refined and the applicability of the process according to the invention further improved.

The cocatalyst used is an aluminoxane of the formula II and/or III, where n is an integer from 0 to 50, preferably 10 to 35.

The radicals R are preferably identical and are methyl, isobutyl, phenyl or benzyl, particularly preferably methyl.

If the radicals R are different, they are preferably methyl and hydrogen or alternatively methyl and isobutyl, hydrogen or isobutyl preferably being present to the extent of 0.01-40% (number of radicals R). The aluminoxane can be replaced as cocatalyst in the polymerization by a mixture comprising aluminoxane and $AlR_3$, where R is as defined above.

The aluminoxane can be prepared in various ways by known processes. One of the methods is, for example, to react an aluminum hydrocarbon compound and/or a hydridoaluminum hydrocarbon compound with water (gaseous, solid, liquid or bound—for example as water of crystallization) in an inert solvent (such as, for example, toluene). To prepare an aluminoxane containing different alkyl groups R, two different trialkylaluminum compounds ($AlR_3 + AlR'_3$), corresponding to the desired composition, are reacted with water (cf. S. Pasynkiewicz, Polyhedron 9 (1990) 429 and EP-A 302 424).

The precise structure of the aluminoxanes II and III is unknown.

Irrespective of the preparation method, all aluminoxane solutions have in common a varying content of unreacted aluminum starting compound, which is in free form or as an adduct.

It is possible, before use in the polymerization reaction, to preactivate the metallocenes, in each case separately or together as a mixture, by means of an aluminoxane of the formula (II) and/or (III). This significantly increases the polymerization activity and improves the particle morphology.

The preactivation of the metallocenes is carried out in solution. The metallocenes are preferably dissolved, as solids, in a solution of the aluminoxane in an inert hydrocarbon. Suitable inert hydrocarbons are aliphatic or aromatic hydrocarbons. Toluene or a $C_6-C_{10}$-hydrocarbon is preferably used.

The concentration of the aluminoxane in the solution is in the range from about 1% by weight to the saturation limit, preferably from 5 to 30% by weight, in each case based on the total solution. The metallocenes can be employed in the same concentration, but are preferably employed in an amount of from $10^{-4}-1$ mole per mole of aluminoxane. The preactivation time is from 5 minutes to 60 hours, preferably from 5 to 60 minutes. The temperature used is from $-78°$ C. to $100°$ C., preferably from $0°$ to $70°$ C.

The metallocenes may also be prepolymerized or applied to a support. Prepolymerization is preferably carried out using the ( or one of the ) olefin( s ) employed in the polymerization.

Examples of suitable supports are silica gels, aluminum oxides, solid aluminoxane or other inorganic support materials. Another suitable support material is a polyolefin powder in finely divided form.

A further possible embodiment of the process according to the invention comprises using a salt-like compound of the formula $R_xNH_{4-x}BR'_4$ or of the formula $R_3PHBR'_4$ as cocatalyst in place of or in addition to an aluminoxane. In these formulae, $x=1$, 2 or 3, $R=$alkyl or aryl, identical or different, and $R'=$aryl, which may also be fluorinated or partially fluorinated. In this case, the catalyst comprises the product of the reaction of the metallocenes with one of said compounds (cf. EP-A 277 004).

In order to remove the catalyst poisons present in the olefin, purification by means of an alkylaluminum compound, for example $AlMe_3$ or $AlEt_3$, is advantageous. This purification can be carried out either in the polymerization system itself, or the olefin is brought into contact with the Al compound before addition to the polymerization system and is subsequently removed again.

The polymerization or copolymerization is carried out in a known manner in solution, in suspension or in the gas phase, continuously or batchwise, in one or more steps, at a temperature of from $-60°$ to $200°$ C., preferably from $20°$ to $80°$ C. Olefins of the formula $R^a$—CH=CH—$R^b$ are polymerized or copolymerized. In this formula $R^a$ and $R^b$ are identical or different and are hydrogen atoms or alkyl radicals having 1 to 14 carbon atoms. However, $R^a$ and $R^b$ may also form a ring with the carbon atoms connecting them. Examples of such olefins are ethylene, propylene, 1-butene, 1-hexene, 4-methyl-1-pentene, 1-octene, norbornene and norbornadiene. In particular, propylene and ethylene are polymerized.

If necessary, hydrogen is added as molecular weight regulator. The various hydrogen-reactivities of the metallocenes and the possibility of changing the amount of hydrogen during the polymerization can result in a further desired broadening of the molecular weight distribution.

The overall pressure in the polymerization system is from 0.5 to 100 bar. The polymerization is preferably carried out in the industrially particularly interesting pressure range of from 5 to 64 bar.

The metallocenes are used in a concentration, based on the transition metal, of from $10^{-3}$ to $10^{-8}$ mol, preferably from $10^{-4}$ to $10^{-7}$ mol, of transition metal per $dm^3$ of solvent or per $dm^3$ of reactor volume. The aluminoxane or the aluminoxane/$AlR_3$ mixture is used in a concentration of from $10^{-5}$ to $10^{-1}$ mol, preferably from $10^{-4}$ to $10^{-2}$ mol, per $dm^3$ of solvent or per $dm^3$ of reactor volume. In principle, however, higher concentrations are also possible.

If the polymerization is carried out as a suspension or solution polymerization, an inert solvent which is customary for the Ziegler low-pressure process is used. For example, the polymerization is carried out in an aliphatic or cycloaliphatic hydrocarbon; the examples of these which may be mentioned are butane, pentane, hexane, heptane, decane, isooctane, cyclohexane and methylcyclohexane. It is also possible to use a gasoline or hydrogenated diesel oil fraction. Toluene can also be used. The polymerization is preferably carried out in the liquid monomer.

If inert solvents are used, the monomers are metered in in gaseous or liquid form.

The polymerization can take as long as desired, since the catalyst system used according to the invention only exhibits a slight decrease in the polymerization activity with time.

The process according to the invention is distinguished by the fact that the metallocenes described give polymers having a broad, bimodal or multimodal molecular weight distribution, high molecular weight, high stereospecificity and good particle morphology in the industrially interesting temperature range between 20° and 80° C. with high polymerization activity.

The polymers according to the invention are particularly suitable for the production of films, in particular transparent films, thermoforming applications, polyolefin foams, extrusion applications and for the production of transparent hollow articles and for blow molding in general.

The examples below are intended to illustrate the invention in greater detail.

The following abbreviations are used:

| | | |
|---|---|---|
| VN | = viscosity number in cm$^3$/g | |
| $M_w$ | = weight average molecular weight in g/mol | determined by gel permeation chromatography |
| $M_w/M_n$ | = molecular weight dispersity | |
| II | = isotactic index (mm + ½ mr) | determined by $^{13}$C-NMR spectroscopy |
| SI | = syndiotactic index (rr + ½ mm) | |
| MFI (230/5) | = melt flow index, measured in accordance with DIN 53735; melt temperature 230° C. and weight 5 kg. | |

EXAMPLE 1

A dry 24 dm$^3$ reactor was flushed with nitrogen and filled with 12 dm$^3$ of liquid propylene. 39 cm$^3$ of a toluene solution of methylaluminoxane (corresponding to 52 mmol of Al, mean degree of oligomerization of the methylaluminoxane was n=19) were then added, and the batch was stirred at 30° C. for 15 minutes.

In parallel, 13.5 mg (0.025 mmol) of rac-phenyl(methyl)silyl(2-methyl-1-indenyl)$_2$zirconium dichloride and 51.0 mg (0.10 mmol) of rac-phenyl(methyl)silyl(1-indenyl)zirconium dichloride were dissolved in 15 cm$^3$ of a toluene solution of methylaluminoxane (20 mmol), and the solution was introduced into the reactor after 15 minutes.

The mixture was polymerized at 30° C. for 3 hours. The polymerization was terminated by addition of 12 1 of CO$_2$ gas. 1.85 kg of polypropylene were obtained, corresponding to an activity of the metallocene mixture of 9.6 kg of PP/g of metallocene×h.

VN=331 cm$^3$/g; $M_w$=411,000 g/mol, $M_w/M_n$=8.5; II=96.9%.

EXAMPLE 2

Example 1 was repeated, but the metallocene mixture components employed were 11.2 mg (0.025 mmol) of racethylene(2-methyl-1-indenyl)$_2$zirconium chloride and 13.9 mg (0.025 mmol) of diphenylmethylene(9-fluorenyl)(cyclopentadienyl) zirconium dichloride; the polymerization temperature was 60° C. and the polymerization time was 1 hour.

2.45 kg of polypropylene were obtained, corresponding to an activity of the metallocene mixture of 97.6 kg of PP/g of metallocene×h.

VN=255 cm$^3$/g; $M_w$=385,000 g/mol, $M_w/M_n$=7.5.

The resultant polymer could be separated by fractionation into a fraction of isotactic polypropylene (II>96%) and a fraction of syndiotactic polypropylene (SI>96%). The mixing ratio was about 1:1.

EXAMPLE 3

Example 1 was repeated, but the metallocene mixture components employed were 5.4 mg (0.010 mmol) of racphenyl (methyl) silyl (2-methyl-1-indenyl)$_2$zirconium dichloride and 5.4 mg (0.013 mmol) of dimethylmethylene(9-fluorenyl) (cyclopentadienyl) zirconium dichloride, the polymerization temperature was 70° C. and the polymerization time was 1 hour.

2.2 kg of a mixture of about two parts of isotactic polypropylene and one part of syndiotactic polypropylene were obtained, corresponding to an activity of the metallocene mixture of 203.7 kg of PP/g of metallocene×h.

VN=172 cm$^3$/g; $M_w$=186,500 g/mol, $M_w/M_n$=3.0.

EXAMPLE 4

Example 1 was repeated, but the metallocene mixture components employed were 4.8 mg (0.01 mmol) of racMe$_2$Si(2-methyl-1-indenyl)$_2$zirconium dichloride and 21.2 mg (0.05 mmol) of rac-Me$_2$Si(2,3,5-trimethyl-cyclopentadienyl)$_2$zirconium dichloride, and the polymerization temperature was 50° C.

2.57 kg of polypropylene were obtained, corresponding to an activity of the metallocene mixture of 32.9 kg of PP/g of metallocene×h.

VN=194 cm$^3$/g; $M_w$=261,000 g/mol, $M_w/M_n$=7.9, II=98.5%.

EXAMPLE 5

Example 1 was repeated, but the metallocene mixture components employed were 4.5 mg (0.008 mmol) of racphenyl(methyl)silyl(2-methyl-1-indenyl)$_2$zirconium dichloride and 6.6 mg (0.015 mmol) of rac-dimethylsilyl(indenyl)2zirconium dichloride. The polymerization time was one hour, and the polymerization temperature was 50° C.

1.35 kg of polypropylene were obtained, corresponding to an activity of the metallocene mixture of 121.6 kg of PP/g of metallocene×h.

VN=154 cm$^3$/g; $M_w$=133,000 g/mol, $M_w/M_n$=5.2, II=96.0%.

EXAMPLE 6

Example 1 was repeated, but the metallocene mixture components employed were 2.4 mg (0.005 mmol) of racdimethylsilyl(2-methyl-1-indenyl)$_2$zirconium dichloride and 2.5 mg (0.005 mmol) of rac-dimethylgermyl(indenyl)$_2$zirconium dichloride. The two metallocenes were dissolved separately, each in 7.5 cm$^3$ of a toluene solution of methylaluminumoxane, and after 15 minutes these solutions were metered into the polymerization system. The mixture was polymerized at 70° C. for 1 hour.

1.57 kg of polypropylene were obtained, corresponding to an activity of the metallocene system of 320.4 kg of PP/g of metallocene$\times$h.

VN=105 cm$^3$/g; $M_w$=114,000 g/mol, $M_w/M_n$=4.1, II=96.3%.

EXAMPLE 7

Example 6 was repeated, but the metallocenes used were 4.8 mg (0.01 mmol) of rac-dimethylsilyl(2-methyl-1-indenyl)$_2$zirconium dichloride and 1.5 mg (0.004 mmol) of rac-dimethylsilyl(indenyl)$_2$dimethylzirconium.

2.08 kg of polypropylene were obtained, corresponding to an activity of the metallocene system of 330.2 kg of PP/g of metallocene$\times$h.

VN=121 cm$^3$/g; $M_w$=101,900 g/mol, $M_w/M_n$=4.0, II=96.0%.

EXAMPLE 8

Example 6 was repeated, but the metallocenes used were 2.7 mg (0.005 mmol) of rac-phenyl(methyl)silyl(2-methyl1-indenyl)$_2$zirconium dichloride and 20.5 mg (0.04 mmol) i 10 of rac-phenyl (vinyl) silyl (indenyl)$_2$zirconium dichloride.

2.17 kg of polypropylene were obtained, corresponding to an activity of the metallocene system of 93.5 kg of PP/g of metallocene$\times$h.

VN=102 cm$^3$/g; $M_w$=79,400 g/mol, $M_w/M_n$=3.3, II=96.9%.

EXAMPLE 9

Example 6 was repeated, but the metallocenes used were 4.8 mg (0.01 mmol) of rac-dimethylsilyl(2-methyl-1-indenyl)$_2$zirconium dichloride and 9.2 mg (0.02 mmol) of

rac-H$_2$C—CH$_2$—CH$_2$—Si(indenyl)$_2$zirconium dichloride.

1.82 kg of polypropylene were obtained, corresponding to an activity of the metallocene system of 130 kg of PP/g of metallocene.

VN=145 cm$^3$/g; $M_w$=185,500 g/mol, $M_w/M_n$=3.6, II=96.8%.

EXAMPLE 10

Example 6 was repeated, but the metallocenes used were 2.7 mg (0.005 mmol) of rac-phenyl(methyl)silyl(2-methyl-1-indenyl)$_2$zirconium dichloride and 2.4 mg (0.006 mmol) of rac-dimethylsilyl(2,4-dimethylcyclopentadienyl)$_2$-zirconium dichloride.

1.31 kg of polypropylene were obtained, corresponding to an activity of the metallocene system of 256.9 kg of PP/g of metallocene$\times$h.

VN=118 cm$^3$/g; $M_w$=129,500 g/mol, $M_w/M_n$=3.8, II=98.0%.

EXAMPLE 11

Example 1 was repeated, but the metallocenes used were 26.9 mg (0.05 mmol) of rac-phenyl(methyl)silyl(2-methyl1-indenyl)$_2$zirconium dichloride and 32.5 mg (0.08 mmol) of rac-dimethylsilyl(2,4-dimethylcyclopentadienyl)$_2$zirconium dichloride. The polymerization time was 2 hours. 2.32 kg of polypropylene were obtained, corresponding to an activity of the metallocene system of 19.5 kg of PP/g of metallocene$\times$h.

VN=386 cm$^3$/g; $M_w$=436,000 g/mol, $M_w/M_n$=7.2, II=98.5%.

EXAMPLE 12

Example 1 was repeated, but the metallocenes used were 9.2 mg (0.02 mmol) of rac-methylethylene(2-methyl-1-indenyl)$_2$zirconium dichloride and 8.6 mg (0.02 mmol) of rac-dimethylmethylene(1-indenyl)$_2$zirconium dichloride, and the polymerization temperature was 50° C. 1.42 kg of polypropylene were obtained, corresponding to an activity of the metallocene system of 26.6 kg of PP/g of metallocene$\times$h.

VN=101 cm$^3$/g; $M_w$=123,000 g/mol, $M_w/M_n$=8.5, II=91.6%.

EXAMPLE 13

A dry 24 dm$^3$ reactor was flushed with nitrogen and filled with 24 dm$^3$ (s.t.p.) of hydrogen and 12 dm$^3$ of liquid propylene.

10 ml of a toluene solution of trimethylaluminum (corresponding to 26 mol of AlMe$_3$) were then added, and the batch was stirred at 40° C. for 15 minutes.

In parallel, 5.4 mg (0.01 mmol) of rac-phenyl(methyl)silyl (2-methyl-1-indenyl )$_2$zirconium dichloride and 4.9 mg (0.01 mmol) of rac-dimethylgermyl(indenyl)$_2$zirconium dichloride were dissolved in 15 cm$^3$ of methylaluminoxane solution (20 mmol of Al, toluene), and, after 15 minutes, the solution was introduced into the reactor. The reactor contents were heated to 65° C. in 3 minutes and polymerized at this temperature for one hour.

The polymerization was terminated by addition of 12 l of CO$_2$ gas, excess propylene was removed in gaseous form, and the polymer powder was dried at 80° C./100 mbar.

2.25 kg of polypropylene were obtained, corresponding to an activity of the metallocene mixture of 218.5 kg of PP/g of metallocene$\times$h.

VN=91 cm$^3$/g; $M_w$=72,800 g/mol, $M_w/M_n$=4.6, II=96.8%.

EXAMPLE 14

Example 1 was repeated, but the metallocenes used were 5.4 mg (0.010 mmol) of rac-phenyl(methyl)silyl(2-methyl-1-indenyl)$_2$zirconium dichloride and 27.0 mg (0.056 mmol) of rac-dimethylsilyl(2-methyl-4,5,6,7-tetrahydro-1-indenyl)$_2$zirconium dichloride, the polymerization temperature was 50° C., and the polymerization time was 1.5 hours.

1.51 kg of polypropylene were obtained, corresponding to an activity of the metallocene system of 31.1 kg of PP/g of metallocene$\times$h.

VN=187 cm$^3$/g; $M_w$=132,500 g/mol, $M_w/M_n$=4.1, II=97.6%.

EXAMPLE 15

Example 1 was repeated, but the metallocenes used were 4.8 mg (0.010 mmol) of rac-dimethylsilyl(2-methyl-1-indenyl)$_2$zirconium dichloride and 7.0 mg (0.017 mmol) of rac-ethylene(1-indenyl)$_2$zirconium dichloride. The polymerization temperature was 50° C. and the polymerization duration was 1 hour.

1.50 kg of polypropylene were obtained, corresponding to an activity of the metallocene system of 127.1 kg of PP/g of metallocene$\times$h.

VN=125 cm$^3$/g; M$_w$=129,500 g/mol, M$_w$/M$_n$=5.3, II=5.4%.

EXAMPLE 16

Example 1 was repeated, but the metallocenes used were 6.0 mg (0.010 mmol) of rac-diphenylsilyl(2-methyl-1-indenyl)$_2$zirconium dichloride, 6.0 mg (0.013 mmol) of rac-dimethylsilyl(1-indenyl)$_2$zirconium dichloride and 36.0 mg (0.083 mmol) of rac-dimethylsilyl(2,3,5-trimethylcyclopentadienyl)$_2$zirconium dichloride, the polymerization temperature was 40° C. and the polymerization duration was 2 hours.

1.79 kg of polypropylene were obtained, corresponding to an activity of the metallocene system of 18.6 kg of PP/g of metallocene$\times$h.

VN=267 cm$^3$/g, M$_w$=293,000 g/mol, M$_w$/M$_n$=5.7, II=98.0%, MFI (230/5)=24.6 g/10 min.

EXAMPLE 17

A dry 24 dm$^3$ reactor was flushed with propylene and filled with 12 dm$^3$ of liquid propylene and with 20 ml of a toluene solution of trimethylaluminum (corresponding to 52 mmol of AlMe$^3$). The batch was stirred at 30° C. for 15 minutes.

In parallel, 3.0 mg (0.005 mmol) of rac-diphenylsilyl(2-methyl-1-indenyl)$_2$zirconium dichloride, 2.0 mg (0.004 mmol) of rac-dimethylsilyl(2-methyl-1-indenyl)$_2$zirconium dichloride and 2.0 mg (0.004 mmol) of rac-dimethylgermyl(1-indenyl)$_2$zirconium dichloride were dissolved in 20 cm$^3$ of methylaluminoxane solution (27 mmol of Al, toluene), and, after 15 minutes, the solution was introduced into the reactor. The mixture was polymerized at 65° C. for 1.5 hours.

1.59 kg of polypropylene were obtained, corresponding to an activity of the metallocene system of 151.4 kg of PP/g of metallocene$\times$h.

VN=153 cm$^3$/g; M$_w$=195,000 g/mol, M$_w$/M$_n$=5.8, II=96.0%, MFI (230/5)=87 g/10 min.

EXAMPLE 18

Example 1 was repeated, but the metallocenes used were 6.0 mg (0.01 mmol) of rac-diphenylsilyl(2-methyl-1-indenyl)$_2$zirconium dichloride and 45.0 mg (0.108mmol) of rac-methylene(3-t-butyl-1-cyclopentadienyl)$_2$zirconium dichloride, the polymerization temperature was 40° C. and the polymerization duration was 4 hours.

1.63 kg of polypropylene were obtained, corresponding to an activity of the metallocene system of 8.0 kg of PP/g of metallocene$\times$h.

VN=358 cm$^3$/g; M$_w$=354,000 g/mol, M$_w$/M$_n$=12.5, II=93.5%.

EXAMPLE 19

Example 1 was repeated, but the metallocenes used were 6.0 mg (0.010 mmol) of rac-diphenylsilyl(2-methyl-1-indenyl)$_2$zirconium dichloride and 6.0 mg (0.012 mmol) of rac-dimethylsilyl(4,7-dimethyl-1-indenyl)$_2$zirconium dichloride, the polymerization temperature was 40° C. and the polymerization duration was 2 hours.

0.85 kg of polypropylene were obtained, corresponding to an activity of the metallocene system of 35.4 kg of PP/g of metallocene$\times$h.

VN=324 cm$^3$/g; M$_w$=352,500 g/mol, M$_w$/M$_n$=15.5, II=95.3%.

EXAMPLE 20

Example 1 was repeated, but the metallocenes used were 6.0 mg ( 0.0 10 mmol ) of rac-diphenylsilyl ( 2-methyl-1-indenyl)$_2$zirconium dichloride and 7.2 mg (0.016 mmol) of rac-ethylene (2-methyl-1-indenyl)$_2$zirconium dichloride.

The polymerization temperature was 50° C. and the polymerization duration was 2 hours.

1.44 kg of polypropylene were obtained, corresponding to an activity of the metallocene system of 54.6 kg of PP/g of metallocene$\times$h.

VN=227 cm$^3$/g; M$_w$=406,000 g/mol, M$_w$/M$_n$=8.0, II=97.1%.

EXAMPLE 21

Example 20 was repeated, but in addition 75 g of ethylene were metered in continuously during the polymerization. The polymerization temperature was 60° C. and the polymerization time was 1 hour.

1.65 kg of ethylene-propylene copolymer were obtained, corresponding to an activity of the metallocene system of 15 125.0 kg of copolymer/g of metallocene$\times$h.

VN=291 cm$^3$/g; M$_w$=387,000 g/mol, M$_w$/M$_n$=7.4; 4.2% ethylene content with ethylene units predominantly incorporated in an isolated manner ($^{13}$C—NMR analysis).

EXAMPLE 22

Example 21 was repeated, but 300 g of ethylene were only added after a polymerization time of 30 minutes.

1.49 kg of copolymer were obtained, corresponding to an activity of the metallocene system of 112.9 kg of copolymer/g of metallocene$\times$h.

VN=357 cm$^3$g; M$_w$=449,000 g/mol, M$_w$/M$_n$=8.8. The polymer product can be separated by fractionation (decane, diethyl ether) into a polypropylene component and an ethylene-propylene rubber component. Ethylene content of the copolymer 18.4%.

EXAMPLE 23

A dry 150 dm$^3$ reactor was flushed with nitrogen and filled at 20° C. with 80 dm$^3$ of a gasoline fraction with the aromatics removed and with a boiling range of 100°–120° C. The gas space was then flushed free from nitrogen by injecting 2 bar of propylene and releasing the pressure, and repeating this cycle four times.

50 l of liquid propylene were added, and 64 cm$^3$ of a toluene solution of methylaluminoxane (corresponding to 100 mmol of Al, molecular weight 990 g/mol according to cryoscopic determination) were added and the reactor contents were heated to 50° C.

Hydrogen was metered in to give a hydrogen content in the gas space of the reactor of 0.1%, and this content was then maintained during the entire polymerization time by topping up (monitoring on-line by gas chromatography).

15.3 mg of rac-methylethylene(2-methyl-1-indenyl)$_2$zirconium dichloride (0.033 mmol), 6.3 mg of racphenyl(methyl)silyl(2-methyl-1-indenyl)₂zirconium dichloride (0.012 mmol) and 7.0 mg of rac-diphenylsilyl(2-methyl-1-indenyl)₂zirconium dichloride (0.012 mmol) were dissolved in 32 ml of a toluene solution of methylaluminoxane (corresponding to 50 mmol of Al) and, after 15 minutes, the solution was introduced into the reactor.

The reactor was kept at a polymerization temperature of 50° C. for 7 hours by cooling, the polymerization was then terminated by addition of 2 bar of $CO_2$ gas, and the polymer formed was separated from the suspension medium in a pressure filter. The product was dried for 24 hours at 80° C./200 mbar. 16.4 kg of polymer powder, were obtained corresponding to a metallocene activity of 81.9 kg of PP/g of metallocene×h.

VN=206 cm³/g; $M_w$=248,000 g/mol; $M_w/M_n$=3.4 II=97.9%; MFI (230/5)=32 g/10 min, m.p.: 151° C.

The product had the following mechanical data: Modulus of elasticity in tension (in accordance with DIN 53457-Z) 1,430 N/mm²; notched impact strength ($a_n$ in accordance with DIN 53453) 5 mJ/mm² at 23° C.; Izod impact strength (in accordance with ISO 180/1 C) 69 mJ/mm² at 23° C. and 12 mJ/mm² at −30° C.; Izod notched impact strength (according to ISO 180/1 A) 3 mJ/mm² at 23° C. and 2 mJ/mm² at −30° C.; ball indentation hardness (pressing, conditioned, 358 N) 84 N/mm² and ball indentation hardness (injection molding, 358 N, in accordance with DIN 53456) 75 N/mm².

EXAMPLE 24

Example 23 was repeated but the metallocene mixture comprised 6.3 mg of rac-phenyl(methyl)silyl(2-methyl-1-indenyl)₂zirconium dichloride (0.012 mmol) and 2.9 mg of rac-dimethylsilyl(1-indenyl)₂zirconium dichloride (0.006 mmol). Polymerization was carried out without hydrogen.

The polymerization was complete after 20 hours.

18.7 kg of polymer powder were obtained, corresponding to a metallocene activity of 101.6 kg of PP/g of metallocene ×h.

VN=202 cm³/g; $M_w$=296,000 g/mol; $M_w/M_n$=7.9 II=96.4%; MFI (230/5)=39 g/10 min; m.p.: 148° C.

The product had the following mechanical data:

Modulus of elasticity in tension (in accordance with DIN 5347-Z) 1,280 N/mm²; notched impact strength ($a_n$ in accordance with DIN 53453) 3 mJ/mm² at 23° C.; Izod impact strength (in accordance with ISO 180/1 C) 65 mJ/mm² at 23° C. and 11 mJ/mm² at −30° C.; Izod notched impact strength (according to ISO 180/1 A) 3 mJ/mm² at 23° C. and 2 mJ/mm² at −30° C.; ball indentation hardness 77 N/mm² (pressing, conditioned, 358 N) and 71 N/mm² (injection molding, 358 N, in accordance with DIN 53 456).

We claim:

1. A process for the preparation of a polyolefin which has a molecular weight distribution $M_w/M_n$ of ≧3.0 and which may be monomodal, bimodal or multimodal, by polymerization or copolymerization of an olefin, consisting essentially of propylene, at a temperature of from −60° to 200° C., at a pressure of from 0.5 to 100 bar, in solution, in suspension or in the gas phase, in the presence of a catalyst comprising a transition-metal component (metallocene) and an aluminoxane of the formula II

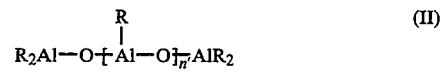

for the linear type and/or of the formula III

for the cyclic type, where, in the formulae II and III, the radicals R are identical or different and are a $C_1$-$C_6$-alkyl group, a $C_1$-$C_6$-fluoroalkyl group, a $C_6$-$C_{18}$-aryl group, a $C_1$-$C_6$-fluoroaryl group or hydrogen, and n is an integer from 0 to 50, or, instead of the aluminoxane, comprises a mixture of an aluminoxane of the formula II and/or of the formula III with a compound $AlR_3$, which comprises using, as the transition-metal component, at least one zirconocene of the formula I and at least one zirconocene of the formula Ia or alternatively at least 2 zirconocenes of the formula I

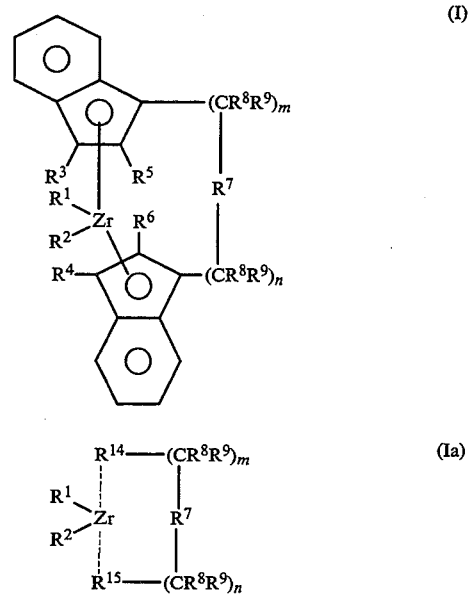

in which

R¹ and R² are identical or different and are a hydrogen atom, a $C_1$-$C_{10}$-alkyl group, a $C_1$-$C_{10}$-alkoxy group, a $C_6$-$C_{10}$-aryl group, a $C_6$-$C_{10}$-aryloxy group, a $C_2$-$C_{10}$-alkenyl group, a $C_7$-$C_{40}$-arylalkyl group, a $C_7$-$C_{40}$-alkylaryl group, a $C_8$-$C_{40}$-arylalkenyl group or a halogen atom, R³ and R⁴ are identical or different and are a hydrogen atom, a halogen atom, a $C_1$-$C_{10}$-alkyl group, which is optionally halogenated, a $C_6$-$C_{10}$-aryl group, or a —NR₂¹⁰, —SR¹⁰, —OSiR₃¹⁰, —SiR₃¹⁰ or —PR₂¹⁰ radical, in which R¹⁰ is a halogen atom, a $C_1$—$C_{10}$-alkyl group or a $C_6$-$C_{10}$-aryl group, R⁵ and R⁶ are identical or different and are as defined for R³ and R⁴ with the proviso that R⁵ and R⁶ are not hydrogen, R⁷ is

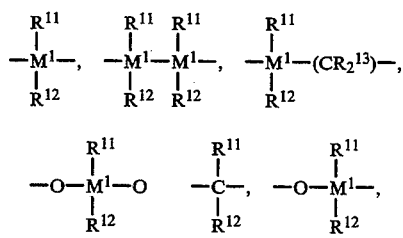

=BR¹¹, =AlR¹¹, —Ge—, —Sn, —O—, —S—,
=SO, =SO₂, =NR¹¹, =CO, =PR¹¹ or
=P(O)R¹¹, where $R^{11}$, $R^{12}$ and $R^{13}$ are identical or different and are a hydrogen atom, a halogen atom, a $C_1$-$C_{10}$-alkyl group, a $C_1$-$C_{10}$-fluoroalkyl group, A $C_6$-$C_{10}$-aryl group, a $C_6$-$C_{10}$-fluoroaryl group, a $C_1$-$C_{10}$-alkoxy group, a $C_2$-$C_{10}$-alkenyl group, a $C_7$-$C_{40}$-arylalkyl group, a $C_8$-$C_{40}$-arylalkenyl group or a $C_7$-$C_{40}$-alkylaryl group, or $R^{11}$ and $R^{12}$ or $R^{11}$ and $R^{13}$, together with the atoms connecting them, in each case form a ring, and $M^1$ is silicon, germanium or tin, $R^8$ and $R^9$ are identical or different and are as defined for $R^{11}$, $R^{14}$ and $R^{15}$ are identical or different and are monocyclic or polycyclic hydrocarbon radicals which can form a sandwich structure together with the zirconium atom, and m and n are identical or different and are zero, 1 or 2, where m plus n is zero, 1 or 2.

2. The process as claimed in claim 1, wherein, in the formula I, $R^1$ and $R^2$ are identical or different and are methyl or chlorine, $R^3$ and $R^4$ are hydrogen, $R^5$ and $R^6$ are identical or different and are methyl, ethyl or trifluoromethyl, $R^7$ is a

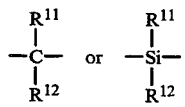

radical, and n plus m is zero or 1.

3. The process as claimed in claim 1, wherein, in the formula Ia,
$R^1$ and $R^2$ are identical or different and are methyl or chlorine,
$R^7$ is a

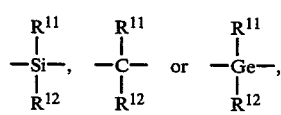

radical,
n+m is zero or 1 and
$R^{14}$ and $R^{15}$ are identical or different and are fluorenyl, idenyl or substituted cyclopentadienyl.

4. The process as claimed in claim 1, wherein propylene is polymerized in combination with a minor amount of ethylene.

5. The process as claimed in claim 1, wherein an isotactic index is in the range of 91.6 to 98.5.

6. The process as claimed in claim 1, wherein $R^3$ and $R^4$ are a hydrogen atom.

7. The process as claimed in claim 1, wherein $R^{11}$, $R^{12}$, and $R^{13}$, are $C_1$-$C_4$-alkyl group, $CF_3$ group, $C_6$-$C_8$-aryl group, pentafluorophenyl group, $C_1$-$C_4$-alkoxy group, $C_2$-$C_4$-alkenyl group, $C_7$-$C_{10}$-arylalkyl group, $C_8$-$C_{12}$-arylalkenyl group, or a $C_7$-$C_{12}$-alkylaryl group.

8. The process as claimed in claim 1, wherein $M^1$ is silicon or germanium.

9. The process as claimed in claim 1, wherein there are either two or three zirconocenes.

10. The process as claimed in claim 1, wherein n' is an integer from 10 to 35.

11. The process as claimed in claim 1, wherein R is methyl.

12. The process as claimed in claim 1, wherein, in said formula II
$R^1$ and $R^2$ are halogen;
$R^5$ and $R^6$ are $C_1$-$C_{10}$-alkyl;
$R^7$ is

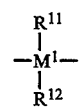

$M^1$ is silicon; and
m and n are zero.

13. A process for the preparation of a monomodal, bimodal, or multimodal polyolefin having a molecular weight distribution $M_w/M_n$ of $\geq 3.0$, comprising:

polymerizing an olefin of the formula $R^aCH=CHR^b$ in which $R^a$ and $R^b$ are identical or different and are a hydrogen atom or an alkyl radical having 1 to 14 carbon atoms, or $R^a$ and $R^b$, together with the atoms connecting them, form a ring, at a temperature for from $-60°$ to $200°$ C., in suspension or in the gas phase, in the presence of a catalyst comprising a zirconocene component and an aluminoxane component, said aluminoxane component comprising an aluminoxane of the formula

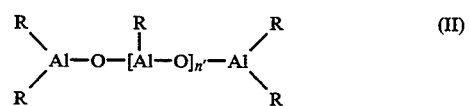

for the linear type or of the formula (III)

for the cyclic type, where, in the formulae II and III, the radicals R are identical or different and are a $C_1$-$C_6$-alkyl group, a $C_1$-$C_6$-fluoroalkyl group, a $C_6$-$C_{18}$-aryl group, a $C_1$-$C_6$-fluoroaryl group or hydrogen, and n' is an number from 0 to 50, said aluminoxane component optionally containing a compound of the formula $AlR_3$; said zirconocene component comprising at least one zirconocene of the formula I and at least one zirconocene of the formula Ia or alternatively at least 2 zirconocenes of the formula I

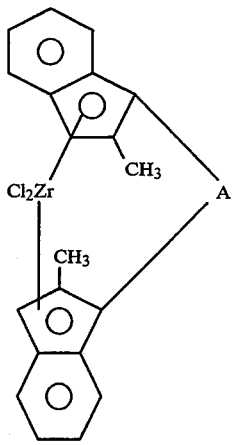  (I)

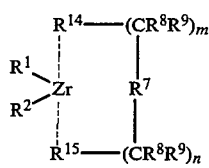

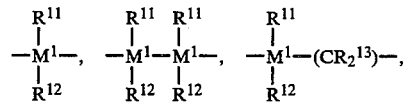  (Ia)

in which
R$^1$ and R$^2$ are identical or different and are a hydrogen atom, a C$_1$-C$_{10}$-alkyl group, a C$_1$-C$_{10}$-alkoxy group, a C$_6$-C$_{10}$-aryl group, a C$_6$-C$_{10}$-aryloxy group, a C$_2$-C$_{10}$-alkenyl group, a C$_7$-C$_{40}$-arylalkyl group, a C$_7$-C$_{40}$-alkylaryl group, a C$_8$-C$_{40}$-arylalkenyl group or a halogen atom, R$^7$ is

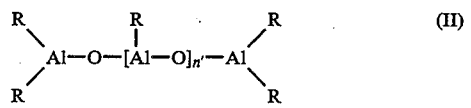

$=$BR$^{11}$, $=$AlR$^{11}$, —Ge—, —Sn, —O—, —S—, $=$SO, $=$SO$_2$, $=$NR$^{11}$, $=$CO, $=$PR$^{11}$ or $=$P(O)R$^{11}$, wherein R$^{11}$, R$^{12}$ and R$^{13}$ are identical or different and are a hydrogen atom, a halogen atom, a C$_1$-C$_{10}$-alkyl group, a C$_1$-C$_{10}$-fluoroalkyl group, a C$_6$-C$_{10}$-aryl group, a C$_6$-C$_{10}$-fluoroaryl group, a C$_1$-C$_{10}$-alkoxy group, a C$_2$-C$_{10}$-alkenyl group, a C$_7$-C$_{40}$-arylalkyl group, a C$_8$-C$_{40}$-arylalkenyl group or a C$_7$-C$_{40}$-alkylaryl group, or R$^{11}$ and R$^{12}$ or R$^{11}$ and R$^{13}$, together with the atoms connecting them, in each case form a ring, and M$^1$ is silicon, germanium or tin, R$^8$ and R$^9$ are identical or different and are as defined for R$^{11}$, R$^{14}$ and R$^{15}$ are identical or different and are a monocyclic or polycyclic hydrocarbon radical which can form a sandwich structure together with the zirconium atom, and m and n are identical or different and are zero, 1 or 2, where m plus n is zero, 1 or 2, and A is ethylene, methylethylene, dimethyl silyl, diphenylsilyl, or phenyl(methyl) silyl.

14. The process as claimed in claim 13, wherein propylene is polymerized, alone or in combination with ethylene.

15. A process for the preparation of a monomodal, bimodal, or multimodal polyolefin having a molecular weight distribution M$_w$/M$_n$ of $\geq 3.0$, comprising:

polymerizing an olefin of the formula R$^a$CH$=$CHR$^b$ in which R$^a$ and R$^b$ are identical or different and are a hydrogen atom or an alkyl radical having 1 to 14 carbon atoms, or R$^a$ and R$^b$, together with the atoms connecting them, form a ring, at a temperature of from $-60°$ to $200°$ C., in suspension or in the gas phase, in the presence of a catalyst comprising a zirconocene component and an aluminoxane component, said aluminoxane component comprising an aluminoxane of the formula

  (II)

for the linear type or of the formula (III)

$$\begin{array}{c} R \\ | \\ {+}Al{-}O{+}_{n'+2} \end{array}$$  (III)

for the cyclic type, where, in the formulae II and III, the radicals R are identical or different and are a C$_1$-C$_6$-alkyl group, a C$_1$-C$_6$-fluoroalkyl group, a C$_6$-C$_{18}$-aryl group, a C$_1$-C$_6$-fluoroaryl group or hydrogen, and n' is a number from 0 to 50, said aluminoxane component optionally containing a compound of the formula AlR$_3$; said zirconocene component comprising at least one zirconocene of the formula I

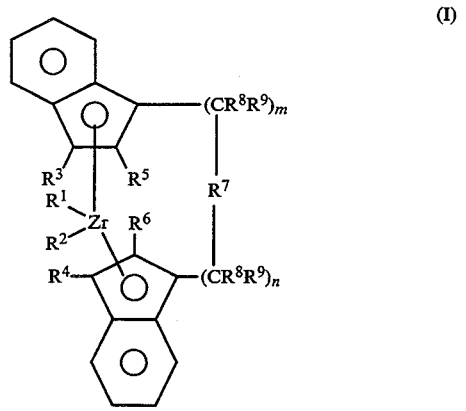  (I)

in which

R$^1$ and R$^2$ are identical or different and are a hydrogen atom, a C$_1$-C$_{10}$-alkyl group, a C$_1$-C$_{10}$-alkoxy group, a C$_6$-C$_{10}$-aryl group, a C$_6$-C$_{10}$-aryloxy group, a C$_2$-C$_{10}$-alkenyl group, a C$_7$-C$_{40}$-arylalkyl group, a C$_7$-C$_{40}$-alkylaryl group, a C$_8$-C$_{40}$-arylalkenyl group or a halogen atom, $R^3$ and $R^4$ are identical or different and are a hydrogen atom, a halogen atom, a $C_1$–$C_{10}$-alkyl group, which is optionally halogenated, a $C_6$–$C_{10}$-aryl group, or a —$NR_2^{10}$, —$SR^{10}$, —$OSiR_3^{10}$, $SiR_3^{10}$ or —$PR_2^{10}$ radical, in which $R^{10}$ is a halogen atom, a $C_1$–$C_{10}$-alkyl group or a $C_6$–$C_{10}$-aryl group, $R^5$ and $R^6$ are identical or different and are as defined for $R^3$ and $R^4$, with the proviso that $R^5$ and $R^6$ are not hydrogen, $R^7$ is

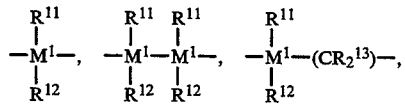

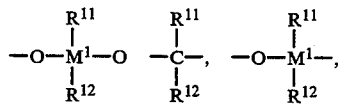

=$BR^{11}$, =$AlR^{11}$, —Ge—, —Sn, —O—, —S—, =SO, =$SO_2$, =$NR^{11}$, =CO, =$PR^{11}$ or =$P(O)R^{11}$, where $R^{11}$, $R^{12}$ and $R^{13}$ are identical or different and are a hydrogen atom, a halogen atom, a $C_1$–$C_{10}$-alkyl group, a $C_1$–$C_{10}$-fluoroalkyl group, a $C_6$–$C_{10}$-aryl group, a $C_6$–$C_{10}$-fluoroaryl group, a $C_1$–$C_{10}$-alkoxy group, a $C_2$–$C_{10}$-alkenyl group, a $C_7$–$C_{40}$-arylalkyl group, a $C_8$–$C_{40}$-arylalkenyl group or a $C_7$–$C_{40}$-alkylaryl group, or $R^{11}$ and $R^{12}$ or $R^{11}$ and $R^{13}$, together with the atoms connecting them, in each case form ring, and $M^1$ is silicon, germanium or tin, $R^8$ and $R^9$ are identical or different and are as defined for $R^{11}$, $R^{14}$ and $R^{15}$ are identical or different and are a monocyclic or polycyclic hydrocarbon radicals which can form a sandwich structure together with the zirconium atom, and m and n are identical or different and are zero, 1 or 2, where m plus n is zero, 1 or 2, and at least one of the following zirconocenes: rac-phenyl(methyl)silyl(indenyl)$_2$zirconium dichloride, diphenylmethylene(9-fluorenyl) (cyclopentadienyl)zirconium dichloride, isopropylidene(9-fluorenyl) (cyclopentadienyl)zirconium dichloride, rac-dimethylsilyl (2,3,5-trimethyl-1-cyclopentadienyl)$_2$zirconium dichloride, rac-dimethylsilyl(indenyl)$_2$zirconium dichloride, rac-dimethylgermyl(indenyl)$_2$zirconium dichloride, rac-dimethylsilyl(indenyl)-2dimethylzirconium, rac-phenyl(vinvl)silyl(indenyl)$_2$zirconium dichloride, rac-H$_2$C—CH$_2$—CH$_2$—Si-(indenyl)$_2$zirconium dichloride, rac-dimethylsilyl (2,4-dimethylcyclopentadienyl)$_2$zirconium dichloride, racisopropylidene(idenyl)$_2$zirconium dichloride, racdimethylsilyl (2-methyl-4,5,6,7-tetrahydro-1-indenyl)$_2$zirconium dichloride, rac-ethylene(indenyl)$_2$zirconium dichloride, rac-methylene(3-t-butyl-1-cyclopentadienyl)$_2$zirconium dichloride and rac-dimethylsilyl(4,7-dimethyl-1-idenyl)-$_2$zirconium dichloride, or alternatively at least two zirconocenes of the formula I.

16. The process as claimed in claim 15, wherein propylene is polymerized, alone or in combination with ethylene.

17. A process for the preparation of a monomodal, bimodal, or multimodal polyolefin having a molecular weight distribution $M_w/M_n$ of $\geq 3.0$, comprising:

polymerizing an olefin of the formula $R^a CH\!=\!CHR^b$ in which $R^a$ and $R^b$ are identical or different and are a hydrogen atom or an alkyl radical having 1 to 14 carbon atoms, or $R^a$ and $R^b$, together with the atoms connecting them, form a ring, at a temperature of from $-60°$ to $200°$ C., in suspension or in the gas phase, in the presence of a catalyst comprising a zirconocene component and an aluminoxane component, said aluminoxane component comprising an aluminoxane of the formula

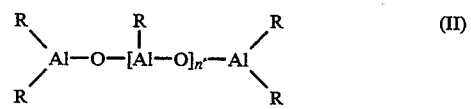

for the linear type or of the formula (III)

for the cyclic type, where, in the formulae II and III, the radicals R are identical or different and are a $C_1$–$C_6$-alkyl group, a $C_1$–$C_6$-fluoroalkyl group, a $C_6$–$C_{18}$-aryl group, a $C_1$–$C_6$-fluoroaryl group or hydrogen, and N' is an integer from 0 to 50, said aluminoxane component optionally containing a compound of the formula $AlR_3$; said zirconocene component comprising at least one zirconocene of the formula I and at least one zirconocene of the formula Ia or alternatively at least 2 zirconocenes of the formula I

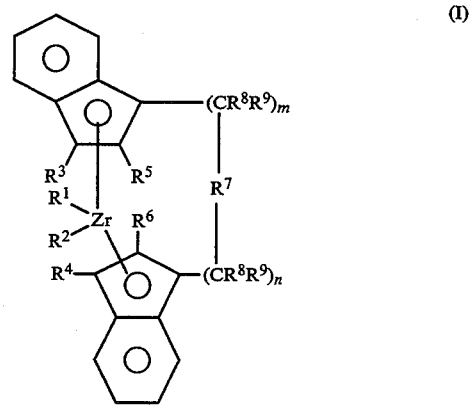

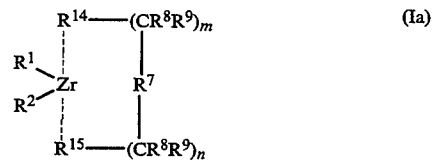

in which $R^1$ and $R^2$ are identical or different and are a hydrogen atom, a $C_1$–$C_{10}$-alkyl group, a $C_1$–$C_{10}$-alkoxy group, a $C_6$–$C_{10}$-aryl group, a $C_6$–$C_{10}$-aryloxy group, a $C_2$–$C_{10}$-alkenyl group, a $C_7$–$C_{40}$-arylalkyl group, a $C_7$–$C_{40}$-alkylaryl group, a $C_8$–$C_{40}$-arylalkenyl group or a halogen atom, $R^3$ and $R^4$ are identical or different and are a hydrogen atom, a halogen atom, a $C_1$–$C_{10}$-alkyl group, which is optionally halogenated, a $C_6$–$C_{10}$-aryl group, or a —$NR_2^{10}$, —$SR^{10}$, —$OSiR_3^{10}$, —$SiR_3^{10}$ or —$PR_2^{10}$ radical, in which $R^{10}$ is a halogen atom, a $C_1$–$C_{10}$-alkyl group or a $C_6$–$C_{10}$-aryl group, $R^5$ and $R^6$ are identical or different and are as defined for $R^3$ and $R^4$, with the proviso that $R^5$ and $R^6$ are not hydrogen, $R^7$ is

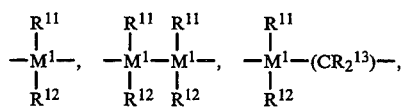

-continued

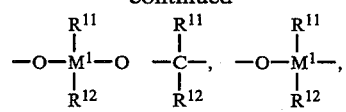

=$BR^{11}$, =$AlR^{11}$, —Ge—, —Sn—, —O—, —S—, =SO, =$SO_2$, =$NR^{11}$, =CO, =$PR^{11}$ or =$P(O)R^{11}$, where $R^{11}$, $R^{12}$ and $R^{13}$ are identical or different and are a hydrogen atom, a halogen atom, a $C_1$–$C_{10}$-alkyl group, a $C_1$–$C_{10}$-fluoroalkyl group, a $C_6$–$C_{10}$-aryl group, a $C_6$–$C_{10}$-fluoroaryl group, a $C_1$–$C_{10}$-alkoxy group, a $C_2$–$C_{10}$-alkenyl group, a $C_7$–$C_{40}$-arylalkyl group, a $C_8$–$C_{40}$-arylalkenyl group or a $C_7$–$C_{40}$-alkylaryl group, or $R^{11}$ and $R^{12}$ or $R^{11}$ and $R^{13}$, together with the atoms connecting them, in each case form a ring, $M^1$ is silicon, germanium or tin, $R^8$ and $R^9$ are identical or different and are as defined for $R^{11}$, $R^{14}$ and $R^{15}$ are identical or different and are monocyclic or polycyclic hydrocarbon radicals which can form a sandwich structure together with the zirconium atom, and m and n are identical or different and are zero, 1 or 2, where m plus n is zero, 1 or 2.

* * * * *

UNITED STATES PATENT AND TRADEMARK OFFICE
CERTIFICATE OF CORRECTION

PATENT NO. : 5,350,817
DATED : September 27, 1994
INVENTOR(S) : Winter, et al.

It is certified that error appears in the above-indentified patent and that said Letters Patent is hereby corrected as shown below:

In column 5, line 25, it should read

--rac-H$_2$C-CH$_2$-CH$_2$-Si(indenyl)$_2$ zirconium dichloride--.

In column 9, line 47 it should read: "rr + 1/2 mm".

In column 10, line 12 it should read: "zirconium dichloride".

In column 11, line 36 please delete "i10".

In column 12, line 34 it should read: "26mmol".

In column 14, line 31 please delete "15".

In column 18, line 15 it should read: "formula I".

Signed and Sealed this

Eighteenth Day of April, 1995

Attest:

BRUCE LEHMAN

Attesting Officer

Commissioner of Patents and Trademarks